United States Patent [19]

Young et al.

[11] Patent Number: 5,512,721
[45] Date of Patent: Apr. 30, 1996

[54] AUTOCLAVABLE ELECTRICAL SWITCH ASSEMBLY FOR USE WITH A MEDICAL DEVICE AND MEDICAL DEVICE USING THE SAME

[75] Inventors: William T. Young, Aptos; Bradley D. Blackwood, Belmont, both of Calif.

[73] Assignee: Unisurge, Inc., Cupertino, Calif.

[21] Appl. No.: 128,309

[22] Filed: Sep. 28, 1993

[51] Int. Cl.⁶ .................................................. H01H 1/10
[52] U.S. Cl. ........................... 200/512; 200/514; 200/308
[58] Field of Search ..................................... 200/292, 512, 200/513–516, 517, 5 A, 293.1, 302.2, 341, 342, 344, 345, 275, 406, 308

[56] References Cited

U.S. PATENT DOCUMENTS

| | | | |
|---|---|---|---|
| Re. 29,440 | 10/1977 | Durkee et al. | 200/5 A |
| 2,200,322 | 5/1940 | Arnesen | 200/293.1 X |
| 3,796,843 | 3/1974 | Durke et al. | 200/5 A |
| 3,952,174 | 4/1976 | Boulanger et al. | 200/5 A |
| 3,988,551 | 10/1976 | Larson | 200/513 X |
| 3,995,128 | 11/1976 | Hawkins | 200/5 A |
| 3,996,427 | 12/1976 | Kaminski | 200/5 A |
| 4,029,916 | 6/1977 | Chu | 200/5 A |
| 4,032,738 | 6/1977 | Esty et al. | 200/308 X |
| 4,083,100 | 4/1978 | Flint et al. | 200/517 X |
| 4,319,099 | 3/1982 | Asher | 200/5 A |
| 4,420,666 | 12/1983 | Kammerer | 200/308 X |
| 4,467,234 | 7/1984 | Bennewitz | 200/512 X |
| 4,545,375 | 10/1985 | Cline | 200/517 X |
| 4,552,143 | 11/1985 | Lottick | 200/293.1 X |
| 4,607,147 | 8/1986 | Ono et al. | 200/512 |
| 4,916,275 | 4/1990 | Almond | 200/516 |

*Primary Examiner*—Renee S. Luebke
*Attorney, Agent, or Firm*—Flehr, Hohbach, Test, Albritton & Herbert

[57] ABSTRACT

An autoclavable electrical switch assembly for use with a medical device having electrical functions comprising a flexible substrate formed of an insulating material and having a first and second surfaces, and having outer margins, first conductive means adherent to the first surface and forming a pattern surrounding an area of the surface and a contact disposed within the area, second conductive means adherent to the second surface and forming a ground plane and at least one, feedthrough means forming a connection between the contact on the first surface and the ground plane on the second surface, a snap dome of a conductive material overlies the contact and engages the pattern surrounding the area, flexible cover means disposed over the first and second surfaces and means for forming a hermetic seal between the outer margins so that the dome is hermetically sealed, said cover means and said hermetic seal being capable of withstanding repeated autoclaving.

11 Claims, 2 Drawing Sheets

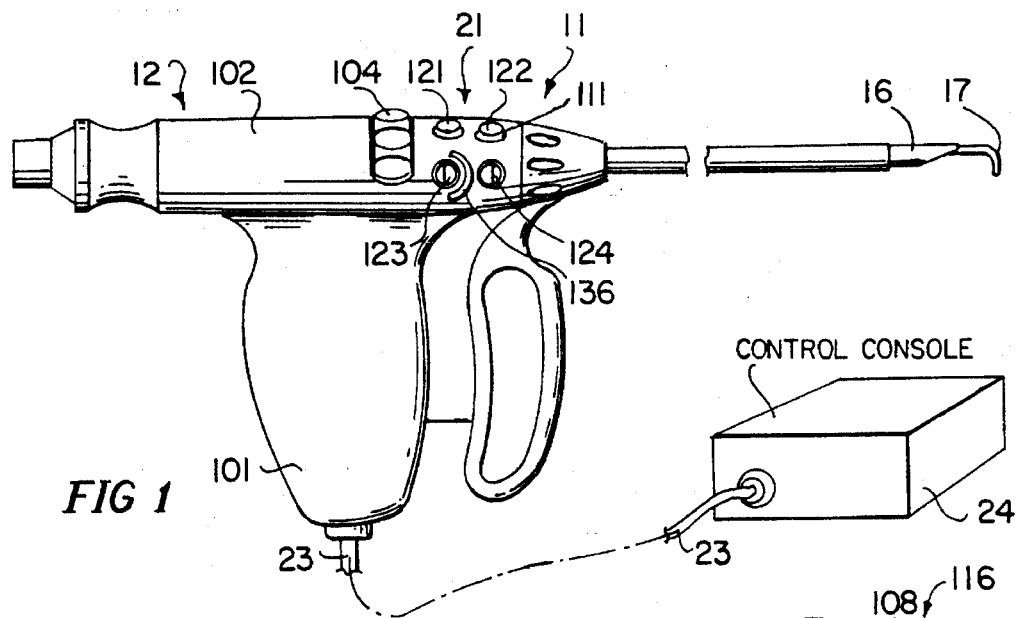
FIG 1
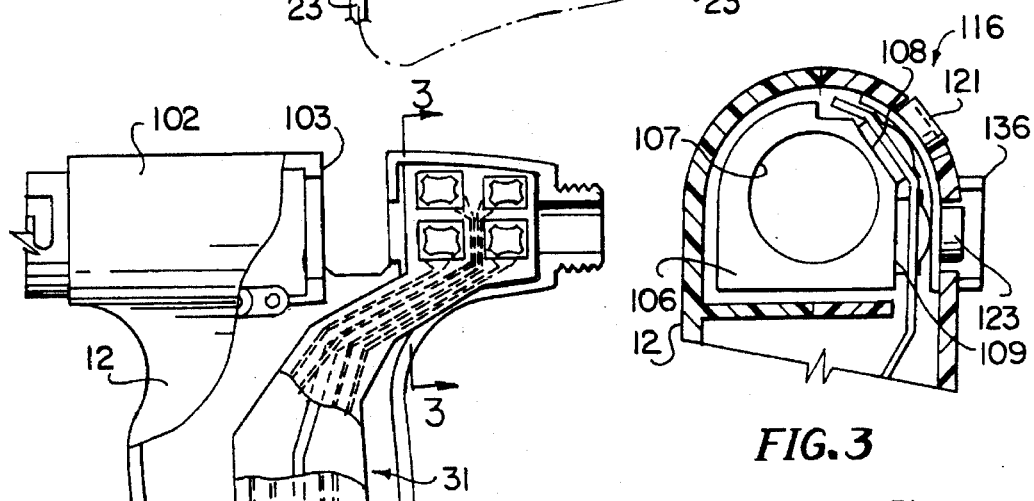
FIG. 2
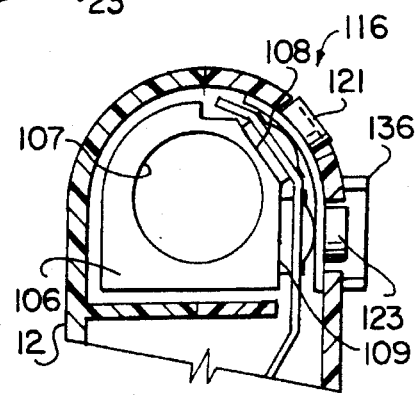
FIG. 3
FIG. 4
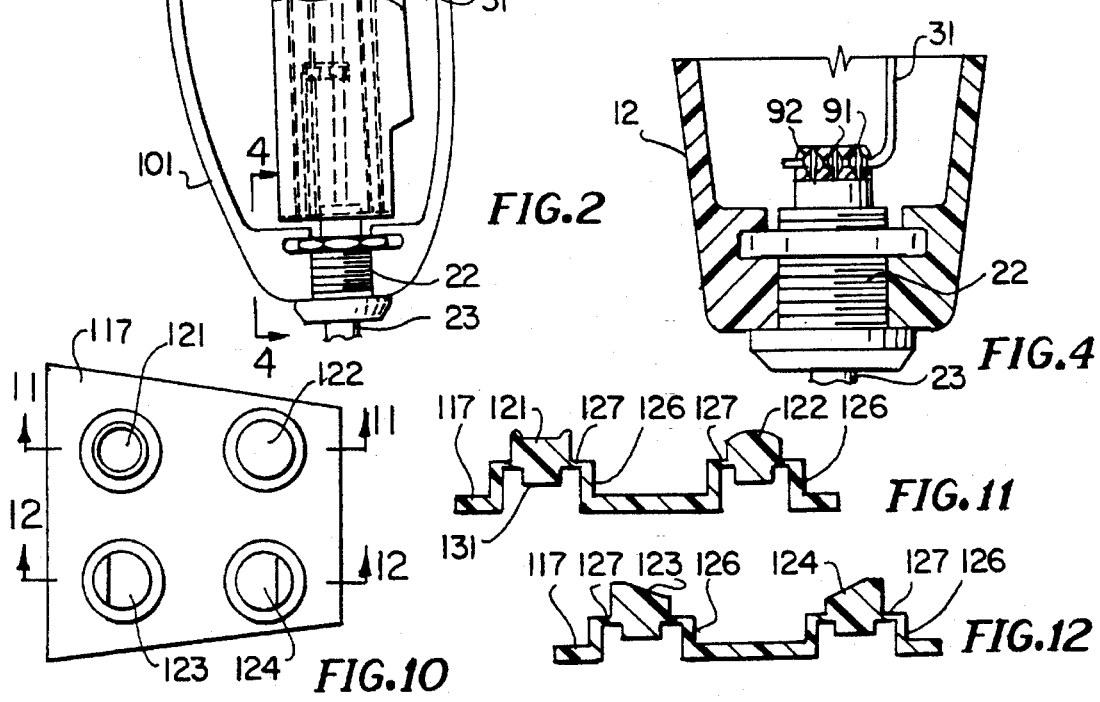
FIG. 10
FIG. 11
FIG. 12

AUTOCLAVABLE ELECTRICAL SWITCH ASSEMBLY FOR USE WITH A MEDICAL DEVICE AND MEDICAL DEVICE USING THE SAME

This invention relates to an autoclavable electrical switch assembly for use with a medical device having electrical functions and a medical device using the same.

In copending application, Ser. No. 07/806,666, filed Dec. 31, 1991, now U.S. Pat. No. 5,433,725, there is disclosed a medical device which has electrical functions and which is utilized in performing laparoscopic procedures. In the electrical switch assembly therein disclosed and to be utilized therewith, it has been found that the electrical switch was incapable of withstanding repeated autoclaving at conventional autoclaving sterilization temperatures of 250° F., 121° C. without random failures occurring. It has been found that the presence of moisture in a switch and the presense of an electrical potential difference between the switch contacts promotes ionic particle migration which eventually will cause the switch to malfunction. There is therefore need for a new and improved autoclavable electrical switch assembly for use with a medical device having electrical functions.

In general, it is an object of the present invention to provide an autoclavable electrical switch assembly which is usable with a medical device having electrical functions.

Another object of the invention is to provide a switch assembly of the above characters which is environmentally sealed and which is resistant to moisture and high temperature.

Another object of the invention is to provide a switch assembly of the above character which is not vented to the atmosphere.

Another object of the invention is to provide a switch assembly of the above character which can withstand numerous cycles of autoclaving.

Another object of the invention is to provide a switch assembly of the above character which is compact and easy to operate.

Another object of the invention is to provide a switch assembly which has the conventional feel of a switch.

Another object of the invention is to provide a switch assembly of the above character which is disposed within a lamination.

Another object of the invention is to provide a switch assembly of the above character in which the lamination is sealed by bonding one plastic to another plastic so as to inhibit delamination.

Additional objects and features of the invention will appear from the following description in which the preferred embodiments are set forth in detail in conjunction with accompanying drawings.

FIG. 1 is a side elevational view of a medical device having electrical functions and using an autoclavable electrical switch assembly incorporating the present invention connected to a control console.

FIG. 2 is an enlarged partial cross-sectional view of the housing shown in FIG. 1 with certain parts broken away to show the electrical switch assembly of the present invention.

FIG. 3 is a cross-sectional view taken along the line 3—3 of FIG. 2.

FIG. 4 is a cross-sectional view taken along the line 4—4 of FIG. 2.

FIG. 10 is a top plan view of a switch actuation insert used in the hand unit of the medical device shown in FIG. 1.

FIG. 11 is a cross-sectional view taken along the line 11—11 of FIG. 10.

FIG. 12 is a cross-sectional view taken along the line 12—12 of FIG. 10.

Figure 5:
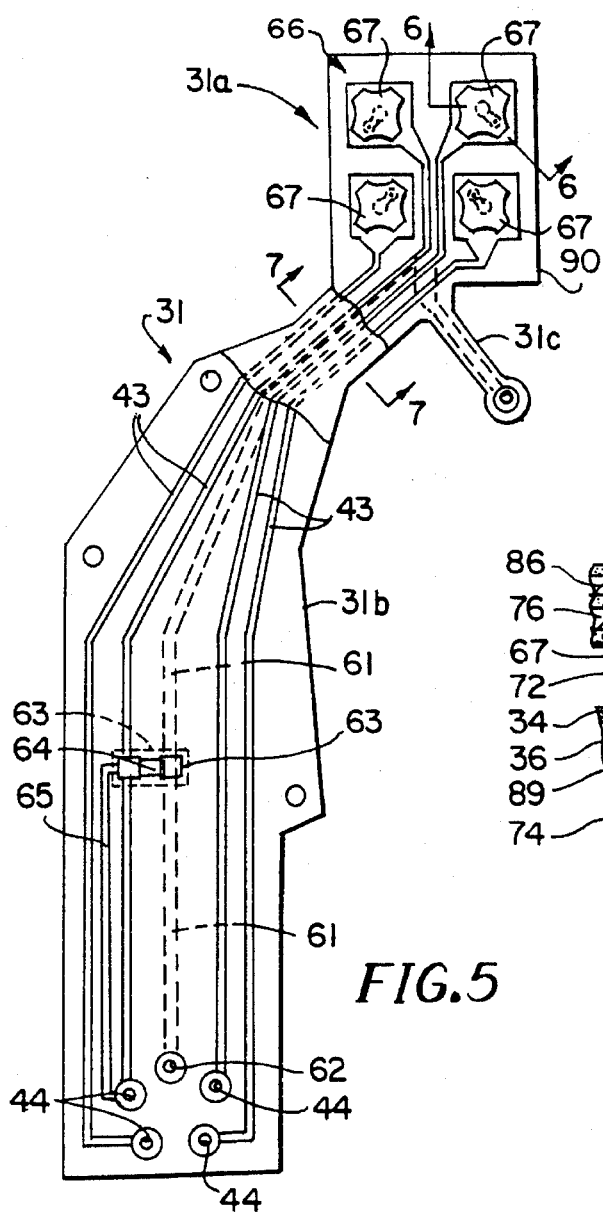
FIG. 5 is a plan view of the electrical flexible strip assembly shown in FIG. 2 before it has been mounted in the housing.
Figure 7:
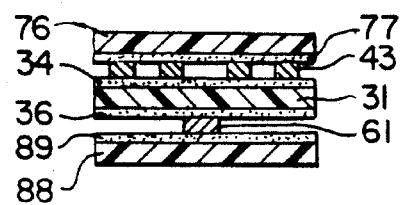
FIG. 7 is a cross-sectional view taken along the line 7—7 of FIG. 5.

In general, the autoclavable electrical switch assembly is for use with a medical device having electrical functions. It is comprised of a flexible substrate formed of an insulating material and having first and second surfaces. First conductive means is provided on the first surface and forms a conductive pattern on said first surface with a first lead extending therefrom. Second conductive means is provided on the second surface forming at least one lead and a pattern connected to said one lead. Feedthrough means is carried by the substrate which extends through the substrate and is connected to the second conductive means. A contact member is disposed on said first side and is spaced from the first conductive means and is connected to the feedthrough means connected to said second conductive means. A domed member formed of a conductive material having a plurality of outwardly extending leg portions makes contact with the pattern of the first conductive means. The central portion of the dome member overlies the contact member whereby when said domed member is depressed it can be moved into contact with the contact member to establish an electrical connection between the first conductive means and the contact member. A flexible cover layer is of insulating material is provided and overlies the domed member and has its outer margin bonded to the outer margin of the flexible substrate to form a hermetic seal therebetween.

More in particular, as shown in FIG. 1, there is provided a medical device 11 generally of the type described U.S. Pat. No. 5,433,725, which consists of a hand unit 12 which has mounted therein a suitable removable tool 16 such an electrocautery "L" hook 17 which is adapted to be utilized with electrocautery operations under the control of switch means 21 incorporated into the hand unit 12. The switch means 21 carried by the hand unit 12 is connected by a circuitry (hereinafter described) which is connected to a connector 22 mounted on the hand unit 12 and connected by flexible cable 23 to a control console 24.

The switch means 21 is the form of a flex circuit which is comprised of a flexible sheet 31 of insulating material formed of a suitable plastic such as Kapton capable of withstanding high temperatures in excess of 250° F., 121° C. As shown, the sheet 31 is in the form of an elongate strip having a head or rectangular portion 31a and a tail portion 31b. It can have a suitable thickness such as 0.001 inches. The sheet 31 is provided with first and second sides 32 and 33. Adhesive layers 34 and 36 are provided on the first and second sides 32 and 33 and have a suitable thickness as per example 0.001 inch. The adhesive which is utilized is typically an acrylic adhesive which can withstand high temperatures in excess of 250° F., 121° C. Copper layers 37 and 38 are provided on the adhesive layers 34 and 36 on the first and second sides 32 and 33 and are formed of a suitable material such as one ounce rolled annealed copper. If desired a greater thickness of copper can be utilized as for example a two ounce rolled annealed copper. Such a copper clad laminate composite can be obtained from Dupont Electronics under the trademark PYRALUX FR. The adhesive used is a flame retardant C-staged acrylic adhesive.

The conductive layers 37 and 38 are photo etched in a conventional manner. The layer 37 is formed into a pattern as shown particularly in FIGS. 5, 6, 7, 8 and 9 of the drawings in which a plurality of surrounding or rectangular enclosures 41 as for example four are provided on the rectangular portion 31a of the sheet 31 which have surrounded rectangular open areas 42 therein to form a narrow trace in a closed loop which is connected to a lead 43 that extends down the tail portion 31b of the sheet 31 and is connected to a plated through hole 44. A centrally disposed contact member 46 is provided within each of the rectangular enclosures 41 and is connected by a conductor or trace 47 (see FIG. 6) to a plated-through hole 48 to make contact with the second copper layer 38.

The second copper layer 38 is also provided with a pattern formed by conventional photo lithographic techniques to provide the two transversely extending rectangular ground planes 51 and 52 (see FIG. 9) which are connected by bridge portions 53. The rectangular ground plane 52 is connected by a lead 56 formed with the pattern which branches off into a lead 57 formed on the sheet 31c and connected to a grounding tab 58. The grounding tab 58 makes contact with a plated-through hole 59. The lead 56 also branches off into another lead 61 which extends along the tail portion 31b of the sheet 31 and terminates in a plated through hole 62.

Spaced apart solder pads 63 are provided on the second surface 33 for mounting a resistor 64. One of the pads 63 is connected to the lead 61 and other pad 63 is connected by a lead 65 on the second surface 33 to a plated-through hole 44 which is connected to one of the leads 43. The resistor 64 operates in connection with the circuitry utilized with the hand unit 12. With the construction shown, the second copper layer serves as a ground plane for the switch contacts hereinafter described. Thus the center contacts 46 are connected to the ground plane.

Figure 6:
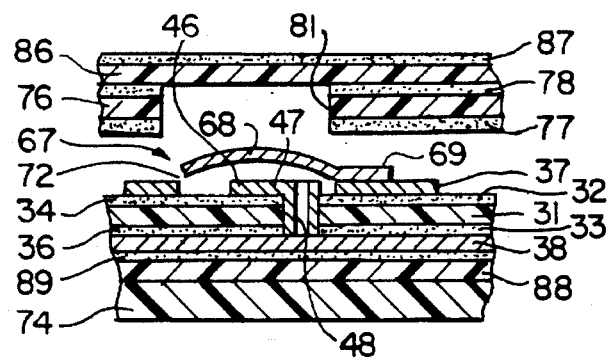
FIG. 6 is a cross-sectional view taken along the line 6—6 of FIG. 5 and of FIG. 8.
Figure 8:
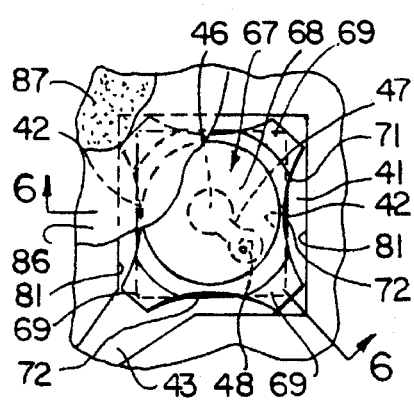
FIG. 8 is a partial plan view of one of the switch assemblies showing the configuration of the first lead means with a snap dome disposed thereabove.

Switch means 66 is provided for forming a connection between the center contact 46connected to ground and the outer margins of the rectangular enclosures 41 which are typically connected to a positive voltage as for example, 5 volts. Such switch means 66 as shown in the drawings comprises a snap dome 67. The snap domes 67 are of a conventional type. The snap domes 67 are preferably rectangular in the form of a square but if desired can be circular or oval in shape. The snap domes 67 are provided with centrally domed portions 68 (see FIG. 8) which are generally rectangular in configuration (see FIG. 9) and are provided with four outwardly extending legs 69 disposed in the corners and spaced approximately 90 degrees apart. They are formed with arcuate cutouts 71 provided in the side margins of the snap dome 67. The leg portions 69 lie generally in a plane with the domed portion 68 extending above the plane. AS can be seen in FIGS. 6 and 8, the snap domes 67 are positioned so that the domed portion 68 overlie the central contacts 46 and are normally spaced therefrom and the leg portions 69 overlie the rectangles 41 and make contact therewith. The arcuate cutouts 71 are sized so they cut slightly into the domed portion 68 and are spaced from the rectangle 41 so that the there is a clearance 72 (see FIG. 6) between the same to permit the flow of gas such as air from under the dome.

In order that no corrosion will occur within the hermetically sealed enclosure provided for the switch contacts hereinbefore described, the portions of the copper pattern which make electrical contact with the snap domes 67 can be plated with nickel to a suitable thickness as for example, 0.00010 inches or greater and thereafter coated with a gold to a thickness of 0.00050 inches in the appropriate locations. Gold has been utilized because it is very resistant to oxidation.

Figure 9:
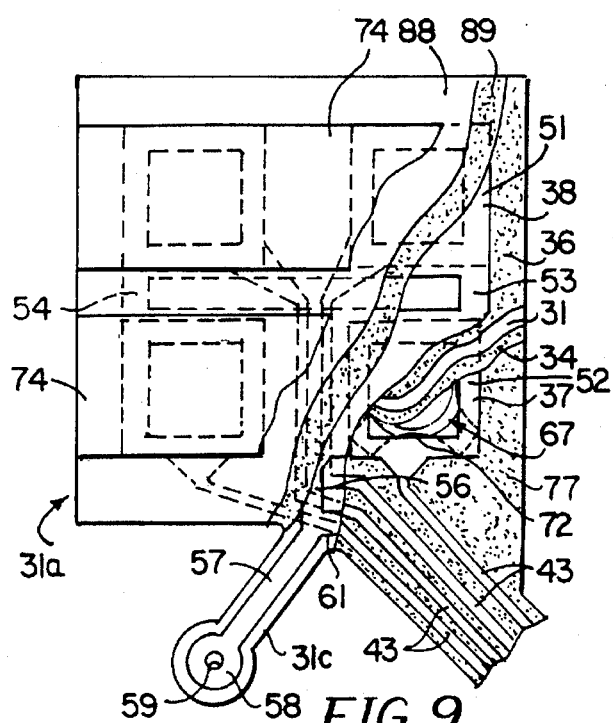
FIG. 9 is a bottom plan view with certain parts broken away showing the second lead means which is utilized for forming a ground connection.

In order to impart a feel to the switch means 21 of the present invention which is similar to that of other pressure actuated switches, support members 74 in the form of stiffeners formed of a suitable material such as epoxy bonded fiberglass can be utilized. As shown in FIG. 9, these stiffeners 74 are substantially co-extensive with the rectangular ground planes 51 and 52 hereinbefore described and underlie the same.

Means is provided for hermetically sealing the snap domes 67 and the contacts hereinafter described engaged thereby and consists of a layer 76 of insulating material of a suitable type such as Kapton and a layer of adhesive 77 adherent thereto both having thicknesses of approximately 0.001 inches. An adhesive layer 78 overlies the Kapton layer 76. The Kapton layer 76 and the adhesive layers 77 and 78 are provided with routed-out rectangular recesses 81 that are sized to accommodate the snap domes 67 and are positioned so that they are in registration with the snap domes 67. An upper cover layer of Kapton 86 with an outwardly facing adhesive layer 87 is provided and is secured to the adhesive layer 78. A lower Kapton cover layer 88 having an adhesive layer 89 thereto is bonded to the copper leads 61 and the adhesive layer 36. The layers 78, 86 and 87b are only provided over the rectangular portion of sheet 31a and do not extend over the tail portion 31b. The layers 76, 77, 78, 86, 87, 88, and 89 all have dimensions slightly larger than the outer margins of the circuitry hereinbefore described so that good bonds or laminations can be obtained between the Kapton cover layers 76, 86 and 88 by the application of pressure at an elevated temperature to provide a hermetic seal extending around the entire outer margin 90 of the circuitry which is shown in FIG. 5. For example, such a high quality lamination can be readily achieved by utilizing suitable pressures as for example, 300 psi at 350 degrees fahrenheit for a period of approximately 30 minutes. During the lamination, care is taken so that lamination does not occur over the top of the snap dome making it possible for air to travel around the edges of the snap dome through the arcuate cut outs. Thus there is relatively free circulation of air as the snap dome is depressed and released by permitting the air to pass through the arcuate cut outs 71. In connection with the lamination, the copper does not extend to the edge of the lamination. This helps to ensure that delamination will not occur. The outer adhesive layer 87 after being cured is no longer tacky.

As shown in FIG. 4, the connector 22 is provided with upstanding pins 91 which are adapted to extend through the plated-through holes 44 and 62 and to be soldered thereon by solder 92 as shown in FIG. 4. Thus it can be seen that one end of the flex circuit which is formed by the sheet 31 is connected to the connector 22 and extends upwardly in the grip 101 of the hand unit 12 which is formed integral with a barrel type housing 102 that is provided with a recess 103 (see FIG. 2) for a thumb wheel 104.

A cylindrical insert 106 formed of a suitable material such as plastic is mounted within the housing just proximal of the recess 103 and is provided with a bore 107 (see FIG. 3). It is also provided with two longitudinally extending closely adjacent flats 108 and 109 which have mounted thereon the stiffeners or support members 74 that are secured thereto by suitable means such as an adhesive (not shown). In this way it can be as seen that the four snap domes 67 which are provided as part of the switch means 21 are disposed on the right side of the grip 101 when the medical device 11 is held in the right hand so that the individual switches formed by the snap domes can be engaged by one of the fingers of the same hand holding the hand unit 12. The barrel 102 is provided with four closely spaced holes 111 which generally overlie the snap domes 67 and which can be appropriately labelled as for example, suction, irrigation, cut and coagulation.

Switch actuation means 116 is provided for actuating the switch means 66 and consists of a sheet-like insert 117 formed of a suitable elastic material such as a silicone. It is formed to provide four switch actuator portions 121, 122, 123 and 124 which are adapted to extend through the holes 111 provided in the barrel as shown in FIG. 1. As shown in FIGS. 12 and 13, the switch portions 122,123 and 124 have different configurations at their top surfaces to provide a different tactile feel to the finger of the hand operating the switches so that the surgeon utilizing the medical device will sense in a tactile manner which switch actuation portion is being engaged by the finger of the hand. Thus, portion 121 has the form of a circular rim (see FIG. 10). Portion 122 is the form of a dome. Portion 123 is in a form of a downwardly and rightly inclined ramp and portion 124 is in the form of a downwardly leftwardly inclined ramp as viewed in FIG. 12. Each of the switch portions 121, 122, 123 and 124 is provided with an upstanding circular flexible portion 126 with an circular portion 127 adjoined thereto and joined to the appropriate switch portion 121, 122, 123 and 124. Each of the portions 121, 122, 123 and 124 is provided with the transversely extending depending bar 131 which is rectangular in cross section which overlies the domed portions 68 of the snap domes 67 so that when a switch actuator portion is depressed by a finger of the hand, the snap dome 68 will be depressed to establish contact between the rectangle 41 carrying the positive voltage and the center contact 46 connected to the ground plane to complete the circuit.

A semicircular raised rim 136 is formed on the barrel 102 and partially encircles the opening 111 for the cut actuator portion. This helps to ensure that the surgeon can sense tactilally that he is engaging the proper actuator portion 123.

Operation and use of the medical device utilizing the switch construction of the present invention may now be briefly described as follows: operation is generally the same as disclosed in U.S. Pat. No. 5,433,725. The individual switches formed by the switch means 61 can be actuated by a finger of the hand as for example, the forefinger of the right hand holding the grip 101 of the hand unit 12 to operate the desired switch by operation of the appropriate switch actuators 121–124. As explained above, the appropriate switch can be tactilally sensed by the finger of the hand as well as observing visually the imprint on the barrel housing 102 as hereinbefore described. Upon depression of the switch actuator, the cross bar 131 engages the snap dome 67 and depresses the same to press the domed portion 68 into contact with the center contact 46 to establish a circuit through the dome legs 69 engaging the rectangular enclosure pattern 41 and through the leads 43 and 61 to the connector 22 and to the instrumentation 24. As the snap dome 67 is depressed, any air or other gas below the snap dome will pass out from under the dome through the clearances 72. When the switch actuator is released, the snap dome 67 will automatically snap back and the encapsulated air will again move under the dome through the arcuate clearances 72. Thus, although the snap dome 67 is completely hermetically encapsulated, the snap dome can readily move between switch closing and opening positions.

It has been found that the hand unit 12 with the switch construction of the present invention incorporated therein can be repeatedly sterilized as for example, by conventional autoclaving techniques using a conventional sterilization temperature of 250° F., 121° C. In such a procedure, it can be submersed in a cleaner for a period of 5 to 10 minutes and then rinsed with distilled water and then autoclaved in a conventional autoclaving cycle. It has been found that the present switch construction can withstand such severe sterilization cycles repeatedly without any delamination occurring and without any failure in the contact structure hermetically enclosed within the lamination. Thus it can be seen that the switch construction of the present invention is environmentally sealed and there is no need to provide additional sealing. The construction is such that it can be manufactured in large quantities relatively economically. The switch construction provides a switch operating feel which is similar to that of conventional pressure operated switches. The switch construction is such that it will always open after the pressure on the same has been released because of the snap domes utilized. The use of a legged snap dome makes it possible for air to readily escape during depression of the switch. Such a construction also ensures that air pockets are not created within the laminated structure.

What is claimed is:

1. An autoclavable electrical switch assembly for use with a medical device having electrical functions comprising a flexible substrate formed of an insulating material and having first and second surfaces capable of withstanding high sterilization temperatures in excess of approximately 250° F. and having outer margins, first conductive means adherent to the first surface and forming a pattern surrounding an area of the surface and a contact disposed within the area, second conductive means adherent to the second surface and forming a ground plane and at least one feedthrough means forming a connection between the contact on the first surface and the ground plane on the second surface, a snap dome of a conductive material overlying the contact and engaging the pattern surrounding the area flexible cover means disposed over the first and second surfaces and means including a high temperature, C-staged acrylic adhesive capable of withstanding high sterilization temperatures in excess of approximately 250° F. for forming a hermetic seal between the flexible cover means and the outer margins to capture the snap dome and to hermetically seal the snap dome, said cover means and said hermetic seal being formed of materials capable of withstanding repeated autoclaving at high sterilization temperatures in excess of approximately 250° F.

2. A switch assembly as in claim 1 wherein said outer margins are free of conductive means.

3. A switch assembly as in claim 2 wherein said snap dome is provided with a centrally disposed opening and wherein said snap dome is provided with arcuate cutouts extending between the legs to provide a clearance for air to pass between the substrate and the snap dome as the snap dome is depressed.

4. A switch assembly as in claim 1 wherein said snap dome is constructed to permit air to pass out from under the snap dome when the snap dome is depressed.

5. A switch assembly as in claim 1 wherein said dome is provided with outwardly extending legs engaging the pattern formed on the first surface.

6. A switch assembly as in claim 1 wherein said cover means is provided with a recess therein overlying the snap dome and adapted to receive the snap dome.

7. A switch assembly as in claim 1 wherein said pattern is continuous and wherein said contact is centrally disposed within said pattern.

8. A switch assembly as in claim 1 wherein a plurality of spaced apart patterns are provided on the first side and the plurality of contacts.

9. A medical device having electrical functions for operation by fingers of a human hand comprising a hand unit adapted to be grasped by the human having having a barrel, and an insert mounted in the barrel and having a bore therein, said insert having circumferentially spaced apart first and second flats thereon, a switch assembly disposed on each of said flats, each of said switch assemblies comprising a flexible substrate formed of an insulating material and having first and second surfaces, first conductive means provided on the first surface and second conductive means provided on the second surface, said first conductive means being formed into a surrounding pattern forming a continuous enclosure and surrounding an area of the first surface and a contact member disposed in the area, means forming a connection between the contact member and the second conductive means, a snap come overlying the contact member and making contact with the surrounding pattern, first and second cover sheets disposed on opposite sides of the snap dome and having outer margins and means hermetically sealing the outer margin so that the snap dome is hermetically sealed therein, said barrel having openings in registration with the switch assemblies and depressible switch actuator means adapted to be engated by a finger of the hand holding the hand unit for causing movement of the snap dome of each switch assembly between contact closed and contact opened positions, said switch actuator means including members extending through the openings in the barrel adapted to be engaged by the finger of the hand.

10. A device in claim 9 wherein each of said switch actuators is provided with a different surface to provide a different tactile feel.

11. A device as in claim 9 together with means for performing a tactile function mounted on the barrel and disposed near at least one of the openings in the barrel.

\* \* \* \* \*